(12) United States Patent
Chappel et al.

(10) Patent No.: US 8,869,826 B2
(45) Date of Patent: Oct. 28, 2014

(54) PASSIVE FLUID FLOW REGULATOR

(75) Inventors: Eric Chappel, Versonnex (FR); Frédéric Neftel, Lausanne (CH)

(73) Assignee: Debiotech S.A., Lausanne (CH)

( * ) Notice: Subject to any disclaimer, the term of this patent is extended or adjusted under 35 U.S.C. 154(b) by 102 days.

(21) Appl. No.: 13/318,669

(22) PCT Filed: May 20, 2010

(86) PCT No.: PCT/IB2010/052250
§ 371 (c)(1),
(2), (4) Date: Nov. 3, 2011

(87) PCT Pub. No.: WO2011/098867
PCT Pub. Date: Aug. 18, 2011

(65) Prior Publication Data
US 2012/0048403 A1    Mar. 1, 2012

(30) Foreign Application Priority Data
May 21, 2009  (EP) .................................... 09160859

(51) Int. Cl.
*F16K 31/12*    (2006.01)
(52) U.S. Cl.
USPC ........................................ 137/504; 251/126
(58) Field of Classification Search
CPC ..... F16K 15/063; F16K 15/02; F16K 15/021; F16K 15/026; A61M 2205/3344; A61M 27/006; A61M 5/16881
USPC .............. 137/544, 516.27, 516.25, 495, 522, 137/528, 538, 504; 251/339, 291, 126
See application file for complete search history.

(56) References Cited

U.S. PATENT DOCUMENTS 2,005,813 A * 6/1935 Thorsen ........................ 137/494
2,977,980 A    4/1961 Scholin
(Continued)

FOREIGN PATENT DOCUMENTS

| EP | 0 414 649 | 2/1991 |
| EP | 0 982 048 | 3/2000 |
| FR | 2 685 206 | 6/1993 |

OTHER PUBLICATIONS

International Search Report for PCT/IB2010/052250, mailed Oct. 19, 2010.
(Continued)

*Primary Examiner* — Eric Keasel
*Assistant Examiner* — Jessica Cahill
(74) *Attorney, Agent, or Firm* — Nixon & Vanderhye P.C.

(57) ABSTRACT

The regulator comprises at least a cylinder (2) with a fluid inlet connector (1) for receiving fluid at an inlet pressure and a fluid outlet connector (4) for delivering fluid, at least one chamber (3), a rod (5) in said cylinder with one side submitted to the inlet pressure and the other side submitted to the outlet pressure generating a net force counter-balanced by at least one spring means (7) acting on one side of said rod (5) against said inlet pressure, wherein a fluidic pathway is formed between said rod (5) and said cylinder (2) as the major fluidic resistance of the device, wherein a change of the inlet pressure induces a move of the rod along the axis of the cylinder thereby modifying the fluidic resistance of said fluidic pathway, wherein the fluidic resistance of said pathway varies with the applied pressure at the inlet in a predefined range of pressure, inducing a regulated flow rate in the considered range of pressure.

23 Claims, 15 Drawing Sheets

(56) References Cited

U.S. PATENT DOCUMENTS

| | | | |
|---|---|---|---|
| 3,122,162 A * | 2/1964 | Sands | 137/498 |
| 3,752,183 A * | 8/1973 | Griswold | 137/504 |
| 3,837,357 A * | 9/1974 | Slaughter, Jr. | 137/554 |
| 3,861,416 A * | 1/1975 | Wichterle | 137/849 |
| 4,176,683 A * | 12/1979 | Leibinsohn | 137/559 |
| 4,675,003 A * | 6/1987 | Hooven | 604/9 |
| 4,682,625 A | 7/1987 | Christopher | |
| 5,054,518 A * | 10/1991 | Rancani | 137/516.27 |
| 5,161,572 A * | 11/1992 | Oberl et al. | 137/516.27 |
| 5,310,094 A * | 5/1994 | Martinez et al. | 222/212 |
| 6,126,628 A * | 10/2000 | Nissels | 604/9 |
| 6,953,325 B2 * | 10/2005 | Weber et al. | 417/222.2 |
| 2005/0016597 A1 * | 1/2005 | Hope et al. | 137/516.27 |
| 2008/0149200 A1 * | 6/2008 | Burkhard et al. | 137/565.11 |
| 2009/0320936 A1 * | 12/2009 | Brunner | 137/533.11 |
| 2010/0004637 A1 * | 1/2010 | Erickson | 604/891.1 |

OTHER PUBLICATIONS

Written Opinion for PCT/IB2010/052250, mailed Oct. 19, 2010.

* cited by examiner illustrates an embodiment of the device comprising a channel in the cylinder illustrates an embodiment of the device comprising a channel parallel to the axis of the cylinder illustrates an embodiment of the device comprising a channel having a variable depth and/or width FIG. 13 illustrates an embodiment of the device comprising a elastomeric ring in the rod FIG. 14 illustrates an embodiment of the device comprising a second spring means (7')

illustrates an embodiment of the device comprising a particle filter (26)

PASSIVE FLUID FLOW REGULATOR

This application is the U.S. national phase of International Application No. PCT/IB2010/052250 filed 20 May 2010 which designated the U.S. and claims priority to EP Patent Application No. 09160859.6 filed 21 May 2009, the entire contents of each of which are hereby incorporated by reference.

TECHNICAL FIELD

The present invention relates to passive flow regulators.

More specifically, the present invention relates to a passive valve for fluid, either liquid or gaseous, with flow self-regulation. The invention more particularly concerns valves of the type used in the field of medical applications, for instance for draining cerebral spinal fluid (CSF) for hydrocephalus patient or/and drug delivery applications. Of course, other applications might be envisaged with the device according to the present invention.

BACKGROUND ART

Hydrocephalus is usually due to blockage of CSF outflow in the ventricles or in the subarachnoid space over the brain. Hydrocephalus treatment is surgical: it involves the placement of a ventricular catheter (a tube made of silastic for example) into the cerebral ventricles to bypass the flow obstruction/malfunctioning arachnoidal granulations and the draining of the excess fluid into other body cavities, from where said fluid can be resorbed.

Most of the CSF shunts have been based on the principle of maintaining a constant intracranial pressure (ICP) regardless of the flow-rate of CSF. The CSF shunts have been constructed to cut off CSF-flow when the differential pressure between the inlet and the outlet of the CSF shunt was reduced to a predestined level, called the opening pressure of the shunt.

An example of an ICP shunt is shown in U.S. Pat. No. 3,288,142 to Hakim, which is a surgical drain valve device used to control the drainage of fluid between different portions of the body of a patient, particularly for draining cerebrospinal fluid from the cerebral ventricles into the blood stream (co called ventriculo-atriostomy).

Clinical experience has proven that this principle of shunting is not an ideal solution. Sudden rises of the ICP, e.g. due to change of position, physical exercise, or pathological pressure waves result in excessive CSF drainage. Several reports in the literature (Aschoff et al., 1995) point at problems due to this overdrainage, and especially the pronounced narrowing of the ventricles has been pointed out as being the main factor leading to malfunctioning of the implanted shunting device. The reason is that the ventricular walls may collapse around the ventricular CSF shunt device, and particles (cells, debris) may intrude into the shunt device.

U.S. Pat. No. 5,192,265 to Drake et al. describes an example of a shunt seeking to overcome the above-mentioned difficulties by proposing a rather complex anti-siphoning device allowing to select transcutaneously the resistance to flow by controlling the pressure in a chamber gas-filled and being in pressure communication with one flexible wall of the main chamber where the flow is regulated.

The use of programmable valves was associated with a reduction in the risk of proximal obstruction and overall shunt revision, one possible explanation for a difference in the two populations studied is that programmable valves may allow the physician to avoid such ventricular collapse by increasing the valve pressure setting after noting clinical signs and symptoms and/or radiological evidence of overdrainage. In this way, proximal obstruction is prevented, and shunt revision surgery is avoided. One such adjustable valve is described in U.S. Pat. No. 4,551,128 to Hakim et al. However, due to the elastomeric properties of the diaphragm material, maintenance of the implanted valve may be required. Further, flow rate adjustment of this adjustable valve after implantation may require a surgical procedure.

Another adjustable valve mechanism, described in U.S. Pat. No. 4,781,673 to Watanabe, includes two parallel fluid flow passages, with each passage including a flow rate regulator and an on-off valve. Fluid flow through the passages is manually controlled by palpably actuating the on-off valves through the scalp. Although the Watanabe device permits flow rate control palpably through the scalp and thus, without surgical intervention, patient and/or physician attention to the valve settings is required.

One system, described in U.S. Pat. No. 6,126,628 to Nissels, describes a dual pathway anti-siphon and flow-control device in which both pathways function in concert. During normal flow, both the primary and secondary pathways are open. When excessive flow is detected, the primary pathway closes and flow is diverted to the high resistance secondary pathway. The secondary pathway decreases the flow rate by 90% while maintaining a drainage rate within physiological ranges, which prevents the damaging complications due to overdrainage. However, this device is intended for use with a shunt system including a valve for controlling flow rate and should be placed distal to the valve inducing cumbersome procedure due to the additional material to be implanted. The system can be used as a stand-alone only for low-pressure flow-control valve.

A valve made of a spring and an arrow-shaped piston moving into a hollow cylinder is described in Patent application EP 0414 649 A2. By increasing the inlet pressure, the piston is moving against the antagonist spring in the cylinder. The piston is made of a conical head 8, a first cylindrical section 11 having a first diameter, a second cylindrical section 10 having a second diameter smaller than the first one and showing a through hole 13 and an internal channel 12, a third cylindrical section 9 having a diameter equal to the first diameter, and finally a last cylindrical section 14 having a diameter small than the first diameter. The first cylindrical section 11 is used to guide the piston 6 in the cylinder 2. The fluid is able to flow in the restriction between the section 11 and the cylinder 2 since the cylinder 2 has a seat 5 with an enlarging triangular shape as shown FIGS. 4 and 5. The fluidic restriction can be seen as a bowed channel having a constant length (equal to the width of the section 11) but a section that increases with the pressure since this section is defined by the triangular shape (5). The depth of the bowed channel is defined by the thickness of the hollow cylinder (2). It is important to note that the main fluidic resistance of the device is said bowed channel has a constant length. The length is defined here according to the Poiseuille's law, i.e. by reference to the direction of the flow. The section of the channel is therefore defined by the normal to the flow direction.

The section 10 is used to collect the fluid via the hole 13 and the internal channel 12 up to the outlet of the device. The channel 12 has a length and a section that do not change with the applied pressure.

The section 9 has only a guiding function and no fluidic action thanks to the large internal channel 12.

By increasing the pressure the fluidic resistance of said channel decreases. By plotting the flow rate against the applied pressure, the slope of the curve is therefore increasing with the pressure, leading to a behaviour similar to other hydrocephalic valves (e.g. Spitz-Holter). This device can be seen as a pressure regulator having a shutoff valve function associated in series with a flow regulator.

Kuffer et al., U.S. Pat. No. 3,674,050 (1972), shows a valve having also a spring, but the fluidic resistance of the channels 10 in FIG. 2 does not vary with the applied pressure.

Griswold, U.S. Pat. No. 3,752,183 (1973), shows a valve having a piston having a shoulder to support the spring action. The piston is not guided along its whole length.

Hooven, U.S. Pat. No. 4,675,003 (1987), shows another hydrocephalus valve having springs but no cylindrical piston.

Christopher, U.S. Pat. No. 4,682,625, provided a shutoff valve having a spring and a cylinder, wherein said cylinder showed several diameters and several guiding areas. The principle is very similar to Patent application EP 0414 649 A2 mentioned above, except for the progressive opening of the fluidic pathway. The main fluidic resistances, i.e. between 120 and 64 or the openings 142 and 144 do not vary with the applied pressure. There is only a change of section from 40 to 64 leading to the opening of the valve after a given pressure threshold that depends on the spring stiffness.

Scholin, U.S. Pat. No. 2,977,980, shows another unidirectional valve very similar to Christopher (U.S. Pat. No. 4,682, 625), having a piston, a cylinder having several diameters and a spring acting on a shoulder of the piston. Once the valve is open, according to Christopher, the fluidic resistance of the device do not depends on the applied pressure.

Roland, French Patent FR 2 685 206 A (Cordis SA), shows a device for hydrocephalus treatment made of a membrane 34 having a calibrated hole 39 that connects the upstream chamber 35 and the downstream chamber 36. The hole 39 is bordered by seals 40 and 41. At low pressure the seal 40 is in contact with the seat 42 inducing a blocking of the flow. By increasing the pressure, the membrane is pushed downward and the fludic pathway is opened between 40 and 42 up to the chamber 36. The distance between the seal 41 and the seat 44 decreases, inducing an annular flow restriction. This annular flow restriction has a fluidic resistance that changes with the applied pressure. The flow restriction can be seen as an annular channel of a constant length (with respect to the flow direction) but having a height decreasing with the pressure. According to the Poiseuille's law, the fluidic resistance of an annular ring varies as the power –3 with the distance between the seal 41 and the seat 44 as for any flat channel while the deflection of the elastic membrane varies linearly with the applied pressure. By design, such device cannot exhibit constant flow rate regulation even by considering two valves in series. Moreover the design is very sensitive to the membrane thickness and tolerances. The use of a spring that can be tested and calibrated before assembly should provide better accuracy than the flexible membrane proposed here. The device does not exhibit guided piston. According to the state of the art, a slit or ball valve having a preloaded spring has been proposed here to regulate the pressure. The principle of a pressure regulator in series with a flow regulator has been already proposed by EP Patent application EP 0 414 649 A2 as discussed previously. The principle of flow regulation by closing gradually a channel has been also proposed by Park which reported a constant flow-rate microvalve for hydrocephalus treatment [S. Park, W. H. Ko, and J. M. Prahl, "A constant flow-rate microvalve actuator based on silicon and micromachining technology," in Tech. Dig. 1988 Solid-State Sens. Actuator Workshop (Hilton Head '88), Hilton Head Island, S.C., Jun. 6-9 (1988) 136-139]. The valve is made of a diaphragm covering a flat substrate; the channel cross-section diminishes under increasing pressure, thus leading to quasi-steady flow-rate. Here again, both theoretical and experimental data reported show that a perfectly steady rate cannot be achieved since the flow resistance should increase with the applied pressure in a linear manner while the variation of the channel cross-section is strongly non-linear. It is clear that the control of the channel shape is fundamental to get an accurate and reproducible flow regulation.

Leonhardt et al., Patent application EP 0 982 048 A1, proposes several methods to monitor intracranial pressure and cerebrospinal fluid flow rate for implantable devices having an active actuator.

SUMMARY OF THE INVENTION

It is therefore an aim of the present invention to improve the known devices and methods.

More specifically, it is an aim of the present invention to propose an auto-regulated valve that overcomes the above-mentioned drawbacks.

A further aim of the present invention is to provide a device that is simple and effective and that can be implanted easily.

Accordingly, the present invention relates generally to a valve that can be used for brain ventricle peritoneum shunt or brain ventricle-auricle shunt surgically to be implanted in the body of a hydrocephalic patient or the like, and more especially, to a brain ventricle shunt which permits to regulate the flow rate of the CSF simulating the physiological CSF resorption independently of the ICP.

As discussed above, differential pressure valves regulate the differential pressure across its ends, i.e. the difference of the pressure captured at the far ends of the catheters, some of these valves also permitting to select one of several possible values of the opening pressure of the valve non-invasively after implantation in order to allow a more flexible handling of the shunt. The main drawbacks of these devices are the so called siphoning effect and the unknown peritoneal pressure changes.

The second effect is related to the fact that the shunt provides a connection between the ventricles of the brain and the peritoneum, the pressure of which being unknown. Therefore, it is impossible to anticipate the intracranial pressure, even if the opening pressure of the shunt is known, thus making it impossible for the surgeon to select the correct opening pressure a priori.

Variable valves regulate the flow of the CSF through the shunt by varying resistance of the valve as a function of the distal pressure. These devices are in principle insensitive to the Siphoning effect, but inherit the problem of necessitating access to atmospheric pressure. As the device is implanted, it makes it sensitive to subcutaneous pressure, which is quite variable, and sensitive to the presence of scar tissues.

A further aim of the present invention is to remedy the inconveniences of the current systems by providing an adjustable resistance valve adapted to be integrated into a shunt system for the treatment of hydrocephalus, the resistance to CSF flow of the valve being self regulated accordingly differential pressure between ICP and resorption site and therefore does not require non-invasive system to be adjusted after implantation as described in U.S. Pat. No. 7,285,296 to Ginggen et al.

As an advantage of the present invention, the flow regulation is more easily achieved with this device made in metal than with other commercial auto-regulated valves in plastics thanks to a better control of the machining tolerances, the simpler design, assembly and testing procedure (Diamond valve, OSV II valve, Orbis sigma valve).

In a first embodiment, the device comprises a valve having a linear functioning mode with respect to the pressure at the inlet side of the valve, with a constant flow rate in a predefined range of pressures.

In another embodiment, the device is a valve with a non linear functioning with respect to the pressure at the inlet side of the valve, with a variable flow rate.

The device according to the invention is defined by the appended claims and will be better understood when considering the following description.

DETAILED DESCRIPTION

Figure 1:
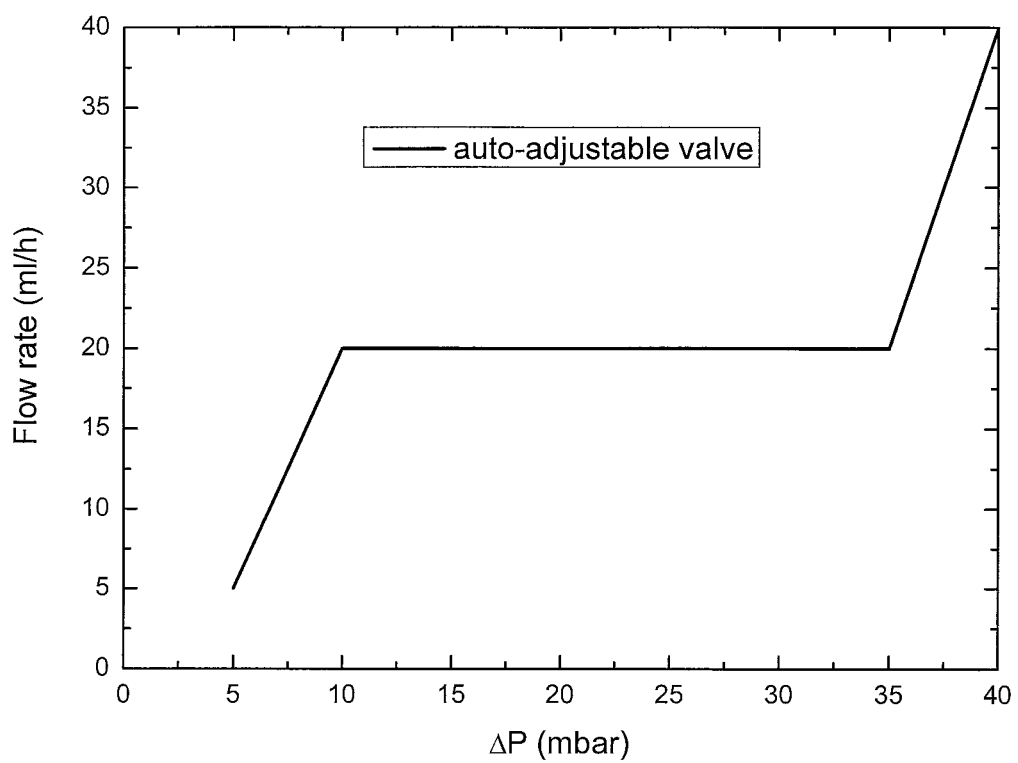
FIG. 1 shows a typical flow rate versus pressure characteristic for passive auto-regulated hydrocephalus valves of the prior art.

FIG. 1 shows a typical flow rate versus pressure characteristic for passive auto-regulated hydrocephalus valves of the prior art.

The flow rate is regulated at 20 ml/h between 10 to 35 mbar. This value corresponds to the mean CSF production of 0.5 L/day. For higher CSF daily volume production, it is necessary to not regulate at high pressure in order to avoid underdrainage. This explains the shape of the curve at high pressure. At low pressure it is no longer necessary to get high flow rate (overdrainage issue). The flow rate can increase linearly from a threshold, which varies from 3 to 10 mbar up to the value of 20 ml/h.

Overdrainages due to patient movement, which induces changes of the hydrostatic pressure, are strongly limited by this flow rate characteristic.

Figure 2:
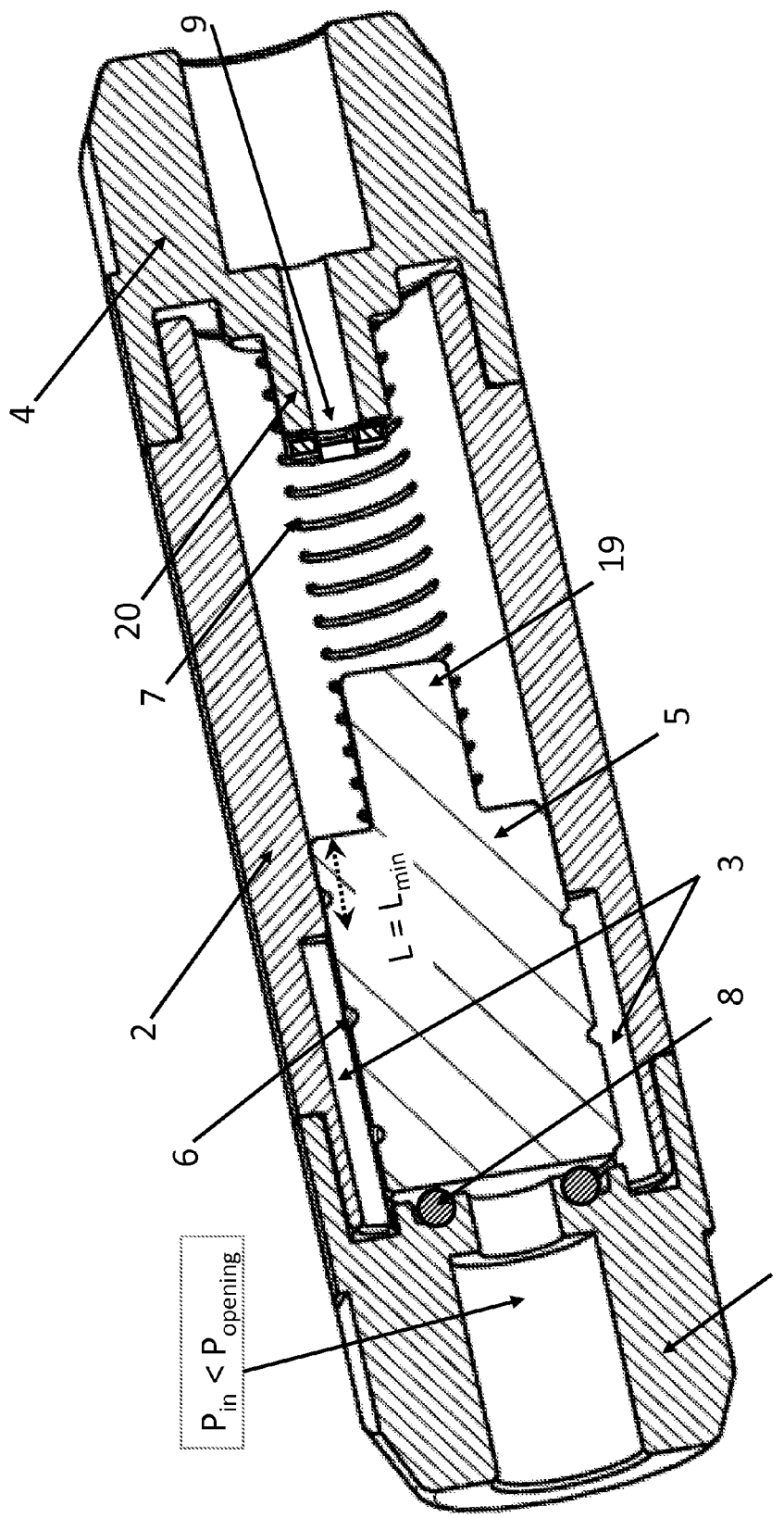
FIG. 2 illustrates an axial cut view of an embodiment of the valve according to the present invention, in a first position.
Figure 3:
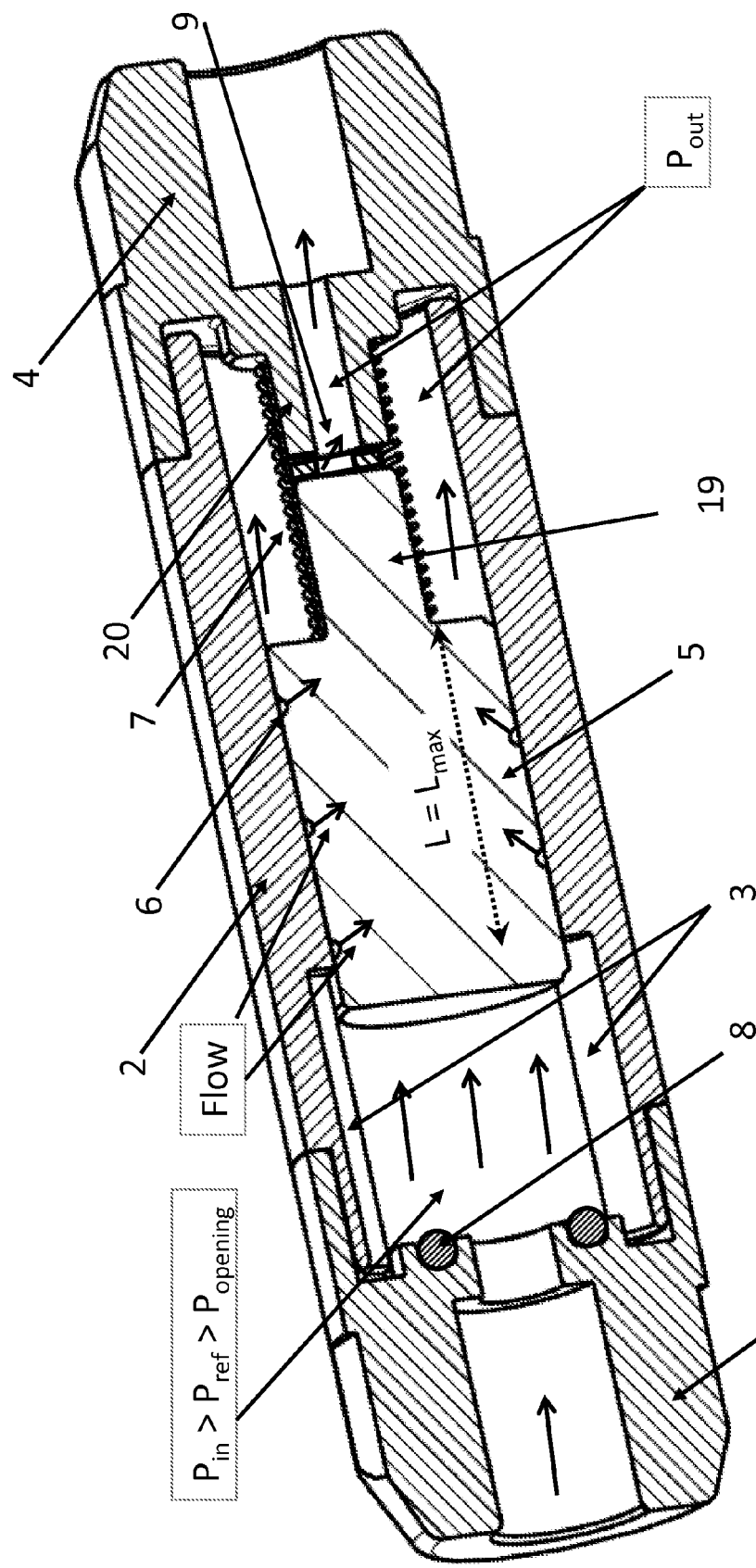
FIG. 3 illustrates an axial cut view of the valve of FIG. 2 in a second position.

FIGS. 2 and 3 illustrate a first embodiment of a valve according to the present invention in cut view and in closed position (FIG. 2) or fully open position (FIG. 3).

The valve comprises in this embodiment an inlet connector 1, a cylinder 2 with cylinder chambers 3 (or openings) and an outlet connector 4. Inside the cylinder 2 there is a rod 5 (or piston) axially movable with a channel 6 (also denominated fluidic channel in the present application), a spring 7, an o-ring 8, an opening 9 in said outlet connector 4, a spring guide in the rod (19) and in the outlet connector (20).

In a first embodiment, the idea is to propose a valve as illustrated in FIG. 2 that has a linear functioning in that it has a constant flow rate Q, independent of the pressure at the inlet side.

The flow rate Q can be written as a function of the difference of pressure $$\Delta P = P_{in} - P_{out};$$
$$Q = \frac{\Delta P}{Rf}.$$

where $R_f$ is the fluidic resistance of the device.

If we ensure that $R_f$ is proportional to $\Delta P$, then $Q$=Constant

The main fluidic resistance of the device illustrated in FIGS. 2 and 3 is the channel 6 of the rod 5. If the section of the channel 6 is constant; then the fluidic resistance in the device is proportional to the length of the channel 6 which is determined by the axial position of the rod 5 in the cylinder 2.

As the pressure increases the rod is displaced axially in the cylinder against the spring 7 and the length of the channel 6 increases thus maintaining a constant flow rate.

Preferably, two chambers 3 are provided in the cylinder 2 to ensure that there is no significant fluidic resistance up to the inlet of the channel 6 while the rod 5 is still guided along its whole length.

Figure 4:
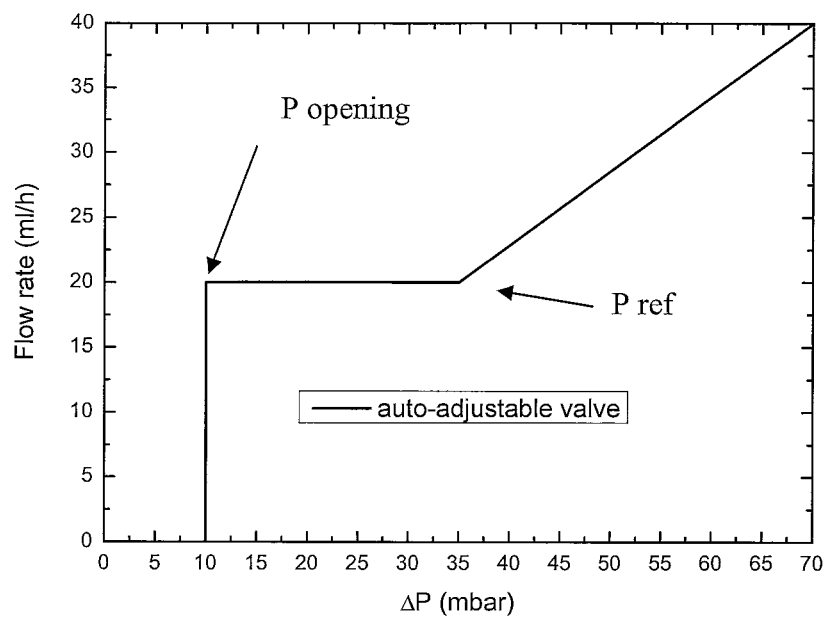
FIG. 4 illustrates the nominal characteristic of the device according to the present invention.
Figure 5:
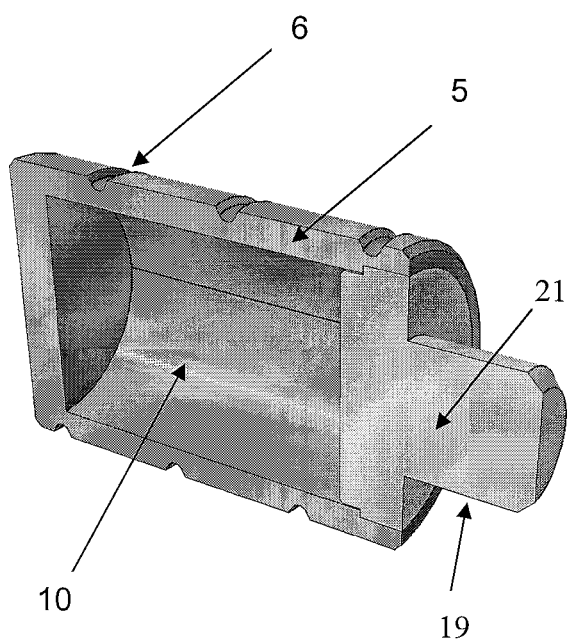
FIG. 5 illustrates a rod according to an embodiment of the present invention.
Figure 5:
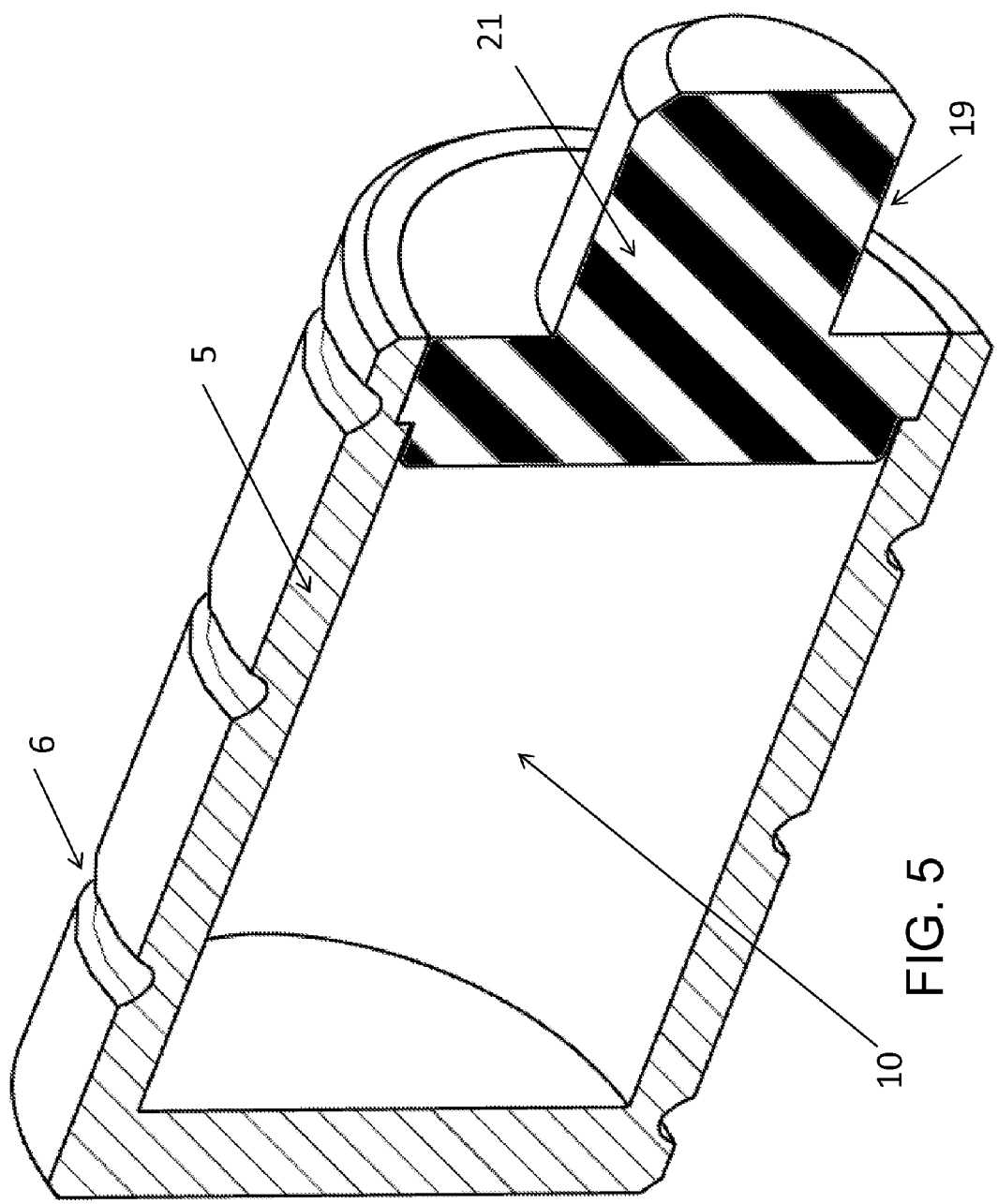

The length of the rod 5 engaged into the cylinder 2 after the openings is noted L (see FIGS. 2 to 4).

For $\Delta P < P_{opening}$, the length L is constant and equal to $L_{min}$.

For $P_{opening} < \Delta P < P_{ref}$, the length L varies linearly with $\Delta P$ thanks to the restoring force of the spring and the regular shape of the channel.

For $\Delta P > P_{ref}$, the length L remains constant and equal to Lmax.

Preferably, the channel(s) should be regular in order to get a constant flow regulator in the range $P_{opening} < \Delta P < P_{ref}$. This can be achieved by a constant depth and width of the channel 6 in addition to a constant pitch of the helix formed by the channel 6 illustrated in FIGS. 2 and 3.

Typically, in variants the channel(s) 6 could be parallel to the rod axis or could be a regular spiral/helix. The channel could be also be made of the annulus formed by the gap between the rod and the cylinder, this gap being defined by the relative sizes of the different parts (outer diameter of the rod 5, inner diameter of the cylinder 2), this even in combination with a channel (straight or spiral etc.).

Of course, the channel 6 could be formed on the rod external surface (as illustrated in FIGS. 2 and 3) and/or on the cylinder internal surface or any equivalent combination.

The tightness of the valve at low pressure is ensured by the pre-load of the spring 7 which pushes the rod 5 against the o-ring 8 located in the inlet connector 1. The system also prevents back-flow as a check valve.

In another embodiment the o-ring 8 can be also attached onto the rod inlet side as well as the opening 9 onto the rod outlet side.

The system may also have chambers 11 (similar to the chambers 3 described above) in the outlet connector for use at high pressure (for $\Delta P < P_{ref}$). The fluidic resistance is then constant in a certain range and a linear increase of the flow with the pressure is expected in this range of pressure. This embodiment is illustrated in FIG. 7 where same parts are identified by the same references as in FIGS. 2 and 3. This device would create a different flow rate profile at high pressure as the one represented in FIG. 6 since at a certain high pressure, when the distal end 6' of the channel 6 ends in said chambers lithe fluidic resistance will diminish the more the pressure increases and the rod moves.

A closing of the fluidic pathway at high pressure may be obtained by replacing the opening 9 of the outlet connector by an o-ring: a sufficiently high pressure will push the rod against this o-ring and thus the flow will be stopped.

As mentioned above, the device can be designed with or without channel 6, depending on the construction and the clearance left between rod 5 and cylinder 2.

With a channel the mechanical adjustment is very tight and thus the leaks are low as well as the effect of rod eccentricity.

Without channel, the entire flow is located between the boring in the cylinder 2 and the rod 5 outer surface. Since the overall gap is larger than with a channel, the centring of the rod 5 in the bore may change during the functioning of the device. A problem of eccentricity induces variation of the flow rate. The larger machining tolerances of this design make that the hardening of the surfaces of the device are probably no longer necessary to avoid any seizing. In any case a hardening of the surfaces may be envisaged.

In a first estimation, the weight of the rod is neglected. A further paragraph is devoted to this issue.

References:
 Spring stiffness=R
 Nominal flow rate $Q_n$=20 ml/h=5.55 $10^{-9}$ m³/s
 Guidance condition: rod length>1.5 rod diameter
 Fluid=water at 37° C.
 Dynamic viscosity=0.7 $10^{-3}$ Pa·s The aim of the following description is mainly to show that a device can be designed with reasonable dimensions and spring stiffness value.

In a first part, description will concentrate on an embodiment of the device without channel and then the description will focus on a embodiment with a channel.

At 35 mbar the fluidic resistance of the device should be:

$$R_f = \frac{3500}{5.5510^{-9}} = 6.310^{11} \text{ Pa.s/m}^3$$

Hypothesis:
 Device length 30 mm
 Ext. diameter 5 mm
 Internal diameter (# bore diam.) 4 mm
 Rod length 12 mm
 Rod stroke length 5.3 mm
 Minimum spring height 4 mm
 Opening pressure=10 mbar $$\text{Force at 35 mbar } F = 3500 \times \pi \times \frac{(4.10^{-3})^2}{4} = \frac{\pi}{100} = 0.044 \text{ N}$$

$$\text{Spring stiffness } R = \frac{0.044}{0.0053} = 8.3 \text{ N/m}$$

Rod ext. diameter 3.964 mm
Compression Spring Dimensioning:
 Material=stainless steel 316L or titanium
 Shear modulus 82000 N/mm² for 316L, 41000 N/mm² for pure titanium and Ti6AV
 2 end coils According to the norm DIN 2089-1 for helical compression cylindrical springs made of wires of circular sections, cold formed, loaded with static or fatigue loading: The ratio D/d should be lower than 20

For a wire diameter d of 0.1 mm the spring diameter should not exceed 2 mm.

Buckling limit: free length $L_0$ of the spring defined by:

$$\upsilon \frac{L_0}{D} \leq 2.5$$

We get $L_0$=10 mm since $\upsilon$=0.5 in our case.
End coils $n_e$=2;
Dead coils $n_d$=0;
Number n of Active Coils:

For 316L $$n = \frac{Gd^4}{8RD^3} = \frac{82000 \times 0.1^4}{8 \times 0.0083 \times 2^3} = 15.5$$

For titanium
 n=7.75
Sum $S_a$ of the Minimum Gaps Between Active Coils:

For 316L $$S_a = n\left(\frac{0.0015D^2}{d} + 0.1d\right) = 1.085 \text{ mm}$$

For titanium
 $S_a$=0.5425 mm
Pitch:

For 316L:

$$m = \frac{L_0 - d(n_e + n_d)}{n} = \frac{9.8}{15.5} = 0.632 \text{ mm}$$

For titanium
 m=1.264 mm

Pre-Load for an Opening Pressure of 10 mbar:

$$\text{Spring initial compression of } \frac{F_0}{R} = \frac{0.044}{3.5 \times 0.0083} = 1.51 \text{ mm}$$

Corrected Max Shear Stress for a Spring of Length L:

$$\sigma_{max} = \frac{8DRk(L_0 - L)}{\pi d^3} \text{ Where } k = \frac{w + 0.5}{w - 0.75}$$

We obtain $\sigma_{max}$=237 N/mm²

This stress is compatible with the yield strength of the following materials:
316LMV: YS=210 N/mm²
Pure titanium grade 1 to 4=>up to YS=520 N/mm² for the grade 4
Ti grade 5 ELI (TiAl6V4 ELI)=>up to YS=800 N/mm²

The data are summarized in the following table, including also 2 other springs of larger wire diameters (5 mil).

|  | Material | 316L | 316L | Ti 4 or Ti 5 | Ti 5 or Ti 5 |
|---|---|---|---|---|---|
| Wire diameter | d (mm) | 0.1 | 0.127 | 0.1 | 0.127 |
| Spring diameter | D (mm) | 2 | 2 | 2 | 2 |
| Spring index | D/d | 20 | 16 | 20 | 16 |
| Free length | $L_0$ (mm) | 10 | 15* | 10 | 10 |
| Nb of active coils | n | 15.5 | 40.32 | 7.75 | 19.145 |
| Nb of end coils | ni | 2 | 2 | 2 | 2 |
| Nb of dead coils | nm | 0 | 0 | 0 | 0 |
| Sum of the minimum gaps between active coils | Sa (mm) | 1.085 | 2.417 | 0.5425 | 1.1768 |
| Min working length | $L_n$ (mm) | 2.835 | 7.79 | 1.5175 | 3.86 |
| Pitch | m (mm) | 0.632 | 0.3657 | 1.264 | 0.5174 |
| Rolling up angle | w (deg) | 5.744 | 3.331 | 11.374 | 4.7075 |
| Developed length | Ld (mm) | 110.45 | 266.34 | 62.24 | 133.27 |
| Corrected max shear stress | N/mm2 | 237 | 120 | 237 | 120 |

*guided spring

Effect of the Rod Eccentricity on the Nominal Flow Rate:

$$\frac{0.0056L}{P\left(a^4 - b^4 - \frac{(a^2 - b^2)^2}{\text{Log}[a/b]}\right)} \bigg/ \frac{0.0056L}{P\left(a^4 - b^4 - \frac{4c^2M^2}{\beta - \alpha} - 8c^2M^2 \times \sum_{n=1}^{1000}\left(n\frac{\text{Exp}[-n(\beta + \alpha)]}{\text{Sin}h[n(\beta - \alpha)]}\right)\right)}$$

According to: F. M. White, Viscous fluid flow, McGraw-Hill 2$^{nd}$ Edition (1991).

The ratio between the flow rate at the eccentricity c and the flow rate in the concentric case writes, for water at 37° C.:
Where a=bore radius; b=rod radius; c=eccentricity;
And $$a = 0.002;\ b = 0.001982;\ L = 0.0053;\ c = d(a - b);$$
$$F = \frac{a^2 - b^2 + c^2}{2c};\ M = \sqrt{(F^2 - a^2)}\ ;\ \alpha = \frac{1}{2}\text{Log}\left[\frac{F + M}{F - M}\right];$$
$$\beta = \frac{1}{2}\text{Log}\left[\frac{F - c + M}{F - c - M}\right];$$

Figure 16:
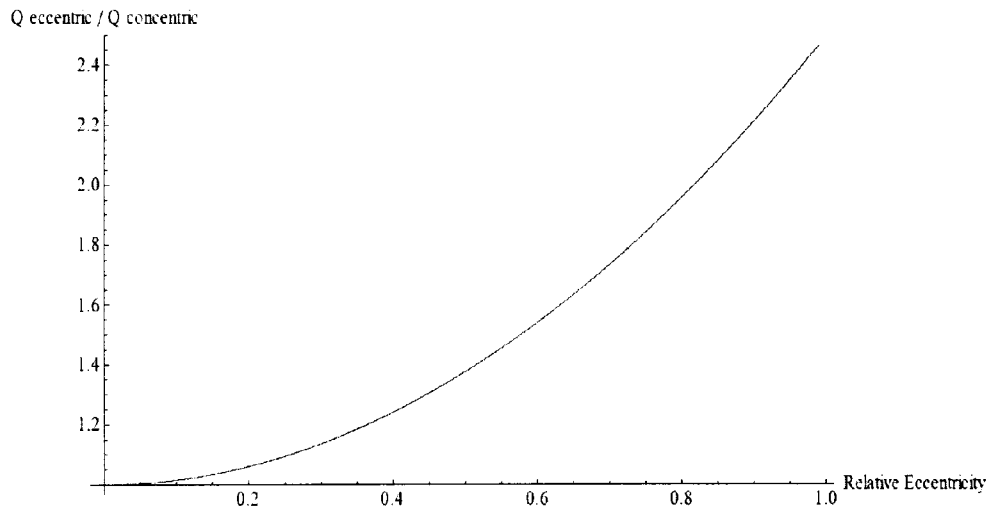
FIG. 16 is a graph of the ratio of flow rates plotted as a function of the relative eccentricity.

In the graph shown in FIG. 16, the ratio is plotted as a function of the relative eccentricity $$\frac{c}{a - b}.$$

The nominal flow may be increased by a factor 2.5 in the worst case. In practice we expect variations of the eccentricity with time that will average the effect as the possible tilt of the rod.

A correction could be useful to take into account this effect, typically by increasing slightly the diameter of the rod.

In the case of a device with channel, the following dimensioning may be made.

The main flow rate through the device is forced to travel in the channel 6 located (preferably but not exclusively) on the rod surface. The tolerances are also very tight in order to limit the leaks.

The cross section of the channel is given by standard machining tool shape: radius of curvature of 0.13 mm and half-angle of 30°.

The linear flow rate resistance, for a depth of penetration of 0.156 mm, is:

$R_f$=1.84478×10$^{13}$ L Pa·s·m$^{-3}$

The channel should also have a length $L_{ch}$ of 34.15 mm for a stroke H=5.3 mm of the rod.

The channel has the shape of a spiral as illustrated in FIGS. 2 and 3. The length of the spiral is:

$$L_s = 2\pi\sqrt{R^2 + b^2}$$

where R is the radius and 2πb the pitch.

The pitch can be calculated as follow:

$$\text{Pitch} = 2\pi b = 2\pi\frac{RH}{\sqrt{L_{ch}^2 - H^2}} = 1.974 \text{ mm}$$

Finally we obtain:

$L_{ch}$=2.685 $L_s$

Figure 17:
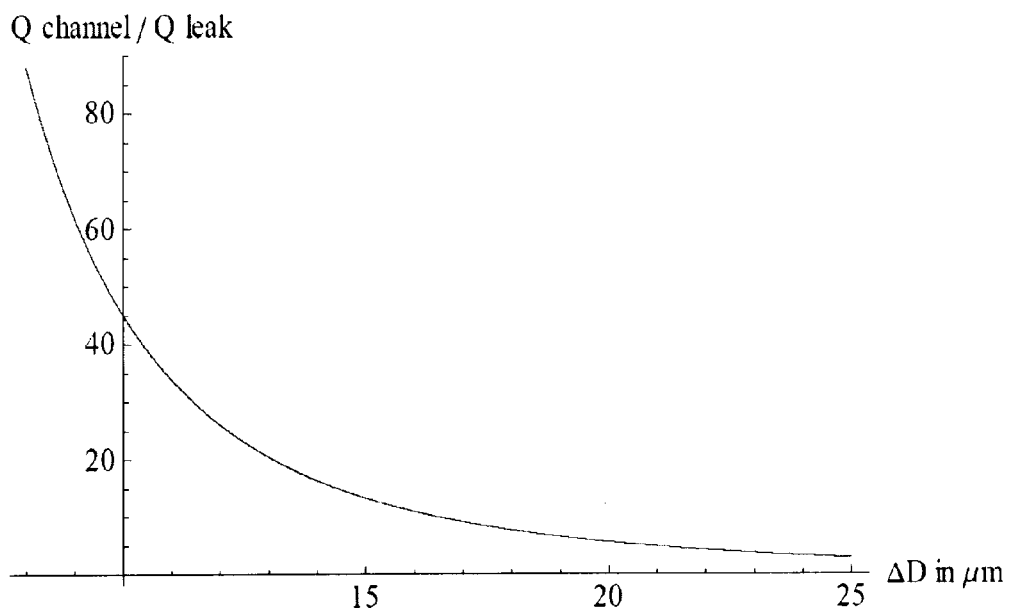
FIG. 17 is a graph showing the ratio between the flow rate in the channel and the leak rate as a function of $\Delta D$

The difference ΔD between the rod and bore diameters has a direct effect on the leak rate. The graph in FIG. 17 shows the ratio between the flow rate in the channel and the leak rate as a function of ΔD.

A maximum ΔD of 16 microns is also allowed for a leak rate lower than 10%.

During use, the rod 5 is not only submitted to pressure forces and spring force but also to its own weight. The weight of the rod 5 makes the device sensitive to its orientation. When the device is vertical, the rod weight increases the compression of the spring. When the rod 5 is horizontal, the rod weight tends to increase the friction force between the rod and the cylinder.

Ideally the rod weight will be completely compensated by Archimedes's force. The rod will be also floating and then the device is no longer sensitive to the orientation.

Since the rod 5 is preferably made of metal, it is desirable to create a cavity 10 filled with gas in the rod 5 and closed by the plug 21. The mean density of the rod should be equal to 1. This feature should also reduce the sensitivity of the device to shocks.

In a variant, in order to avoid any blocking issue due to a shock for instance, one can easily implement a second spring on the top of the rod 5, i.e. on the side of the rod without a spring. One can also attach the single bottom spring 7 to the housing and to the rod but this makes the assembly more difficult. It is of course necessary to include this additional force during the device dimensioning.

The tightness at low pressure is obtained using an o-ring and/or a ball. Above 35 mbar the fluidic resistance of the system is constant in order to prevent underdrainage.

The profile of the flow regulation (flow rate versus pressure characteristic) given in FIG. 4 is a typical example for an adult patient.

However, different profiles may be desirable. For example, the mean flow rate could be adapted to the patient but also the shape of the profile.

Typically, according to the present invention, the shape of the Q(ΔP) curve can be adjusted by changing the channel parameters, for example its depth or width and its pitch for the case of a spiral channel.

The rod may also present sections with a channel and sections without channel. Both channel depth and pitch may be also modulated.

Figure 6:
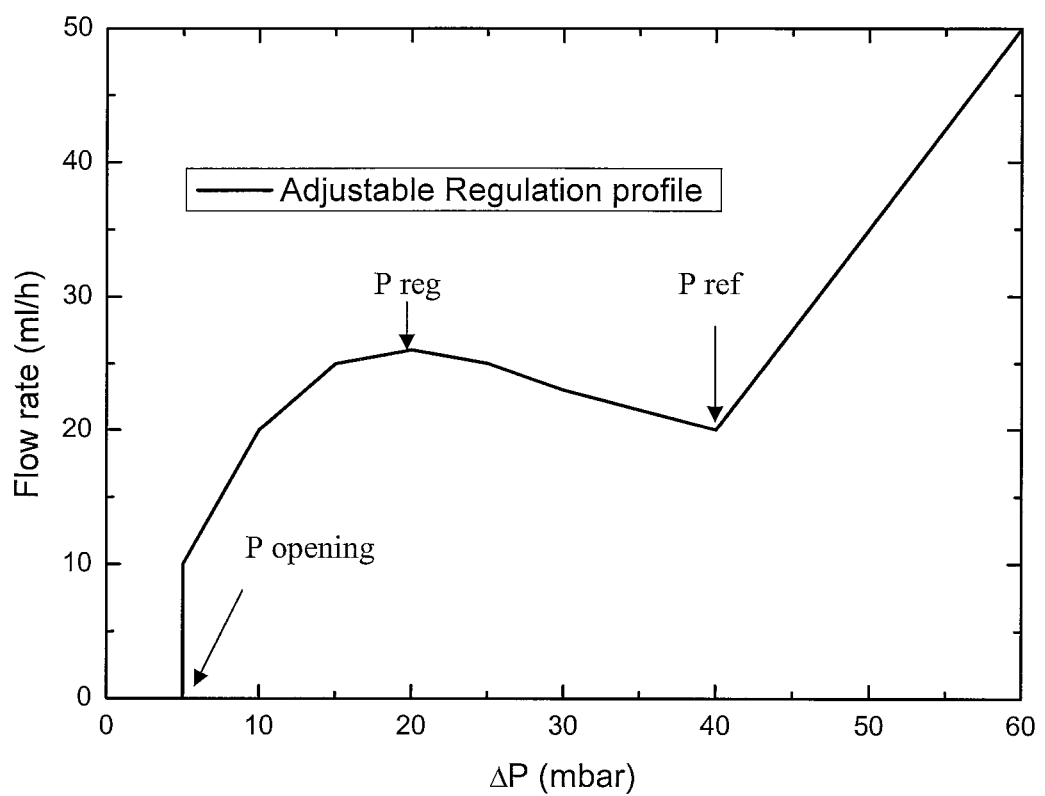
FIG. 6 illustrates another regulation profile of an embodiment of the present invention.
Figure 7:
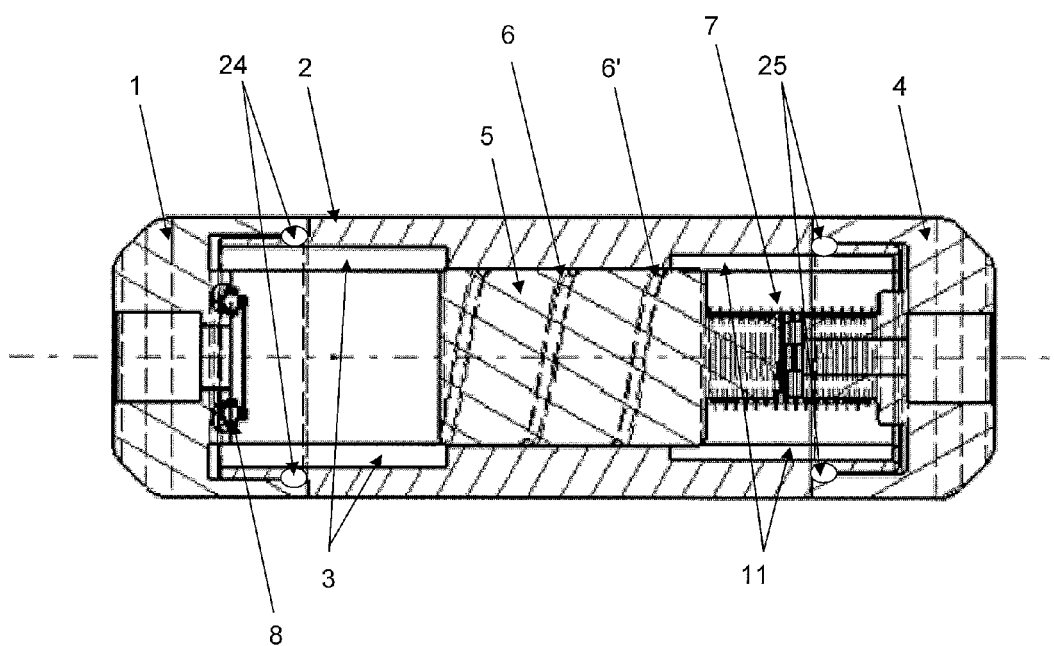
FIG. 7 illustrates an embodiment of the device according to the present invention.

FIG. 6 illustrates an example of regulation profile that limits the high pressures due to excess of CSF production:

Since the production rate of CSF is not constant, it could be very interesting to have the profile shown in FIG. 6: the mean flow rate remains centred around 20 ml/h, but any increase in the CSF production will be counterbalanced by an increase of the flow rate (in the low pressure range-cusp in the previous curve). One can also limit the increase of pressure by this means. The system remains anti-siphoning thanks to the limitation of the flow rate at medium pressure, typically when the patient is in a vertical position. At higher pressure rate the system allows increase of flow rate to prevent any underdrainage.

The regulation profile 6 has therefore 4 phases:
1. For $\Delta P < P_{opening}$ the system is tight and prevents back-flow as well as overdrainage.
2. For $P_{opening} < \Delta P < P_{reg}$, the flow rate increases with the pressure up to a maximum at $P = P_{reg}$ to limit the underdainage and also to limit the intracranial pressure of the patient during abnormal CSF production.
3. For $P_{reg} < \Delta P < P_{ref}$ the flow rate decreases with the pressure up to a minimum, typically at $P_{ref}$, to prevent siphoning effect.
4. For $\Delta P > P_{ref}$ the flow rate increases with the pressure to prevent underdrainage.

At high pressure, the device can be designed to:
have a constant fluidic resistance and thus a constant slope Q(ΔP) as described above
have a shutdown system, typically by blocking the flow by an o-ring at the outlet when the pressure pushes the rod against the outlet connector; or by blocking the flow at the beginning of the channel (inlet side) if the channel is not machined over the entire length of the rod In addition, the slope of the Q(ΔP) curve can be increased at high pressure if openings or chambers 11 in the cylinder are machined also at the outlet side. The fluidic resistance can become very small by this means (see FIG. 7). The fluid is forced to travel through the channel only between the parts located between the openings 3 and 11 of the cylinder placed at the inlet and the outlet since the pressure in these openings can be considered constant.

These openings 11 are similar to those at the inlet (openings or chambers 3): they have not the cylindrical symmetry otherwise the guiding of the rod will be lost along this machined section. The length of the openings 11 is adjusted to the required flow versus pressure characteristics that is desired.

At high pressure and by design, different options can be therefore chosen:
a free flow
a flow restriction
a shutdown valve As can be understood from the above description and the drawings, by design the system prevents the back-flow thanks to the pre-load of the spring which ensures the tightness by pushing the rod against the o-ring of the inlet port.

In a variant, it is possible to provide means, for example external means that allow adjustment of said preload.

Also, in another variant, one may add external means that allow changing the position of the rod in the cylinder. Typically, such means are useful to unblock the rod in the event of a blockage.

All parts have been designed to be produced by low cost standard machining, typically by undercutting.

The external part of the rod as well as the internal part of the cylinder should be polished and a surface hardening may be necessary to reduce the probability of the rod 3 binding.

The inlet and outlet ports 1, 4 which are tightly connected to the catheters can be made in metal or in plastic. They can be attached to the cylinder 2 by any suitable means (i.e gluing force fitting etc) reversible or not.

The system exhibits very interesting features in term of assembly. The diameters of the rod and the cylinder can be obtained using standard tools for metrology (optical . . . ).

By contrast to other flow regulator system, the elastic part of the system (the spring) can be tested independently. It is also possible to match the rod/cylinder to the spring. The assembly is moreover reversible.

The system can be tested automatically by using a pressure controller connected to the inlet and a gas flowmeter at the outlet.

The tightness of the system, when the inlet and the outlet are closed, should be also tested (tightness of the connectors that could be soldered or glued . . . ).

The opening pressure of the device depends directly on the spring pre-load. The pre-load of the spring can be adjusted during the production but also during the functioning of the device.

Figure 9:
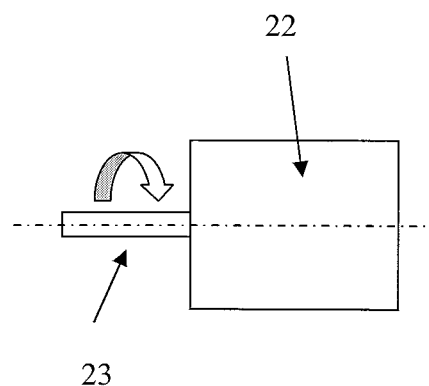
FIG. 9 illustrates schematically a rotary motor that can be coupled to the outlet connector in an embodiment of the present invention.
Figure 10:
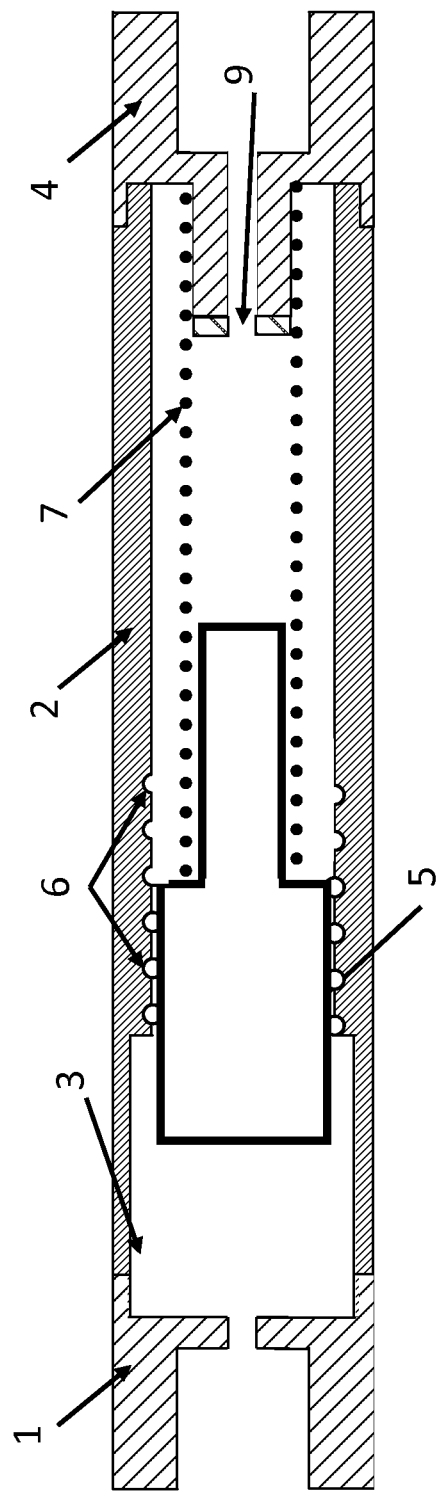
FIG. 10 illustrates an embodiment of the device comprising a channel in the cylinder.
Figure 11:
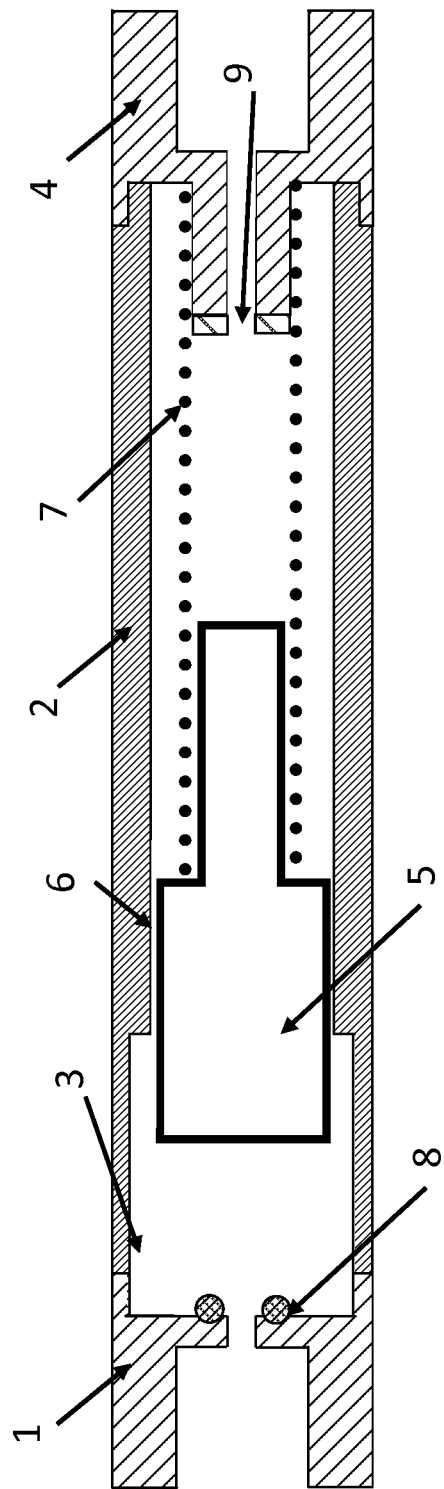
FIG. 11 illustrates an embodiment of the device comprising a channel parallel to the axis of the cylinder.
Figure 12:
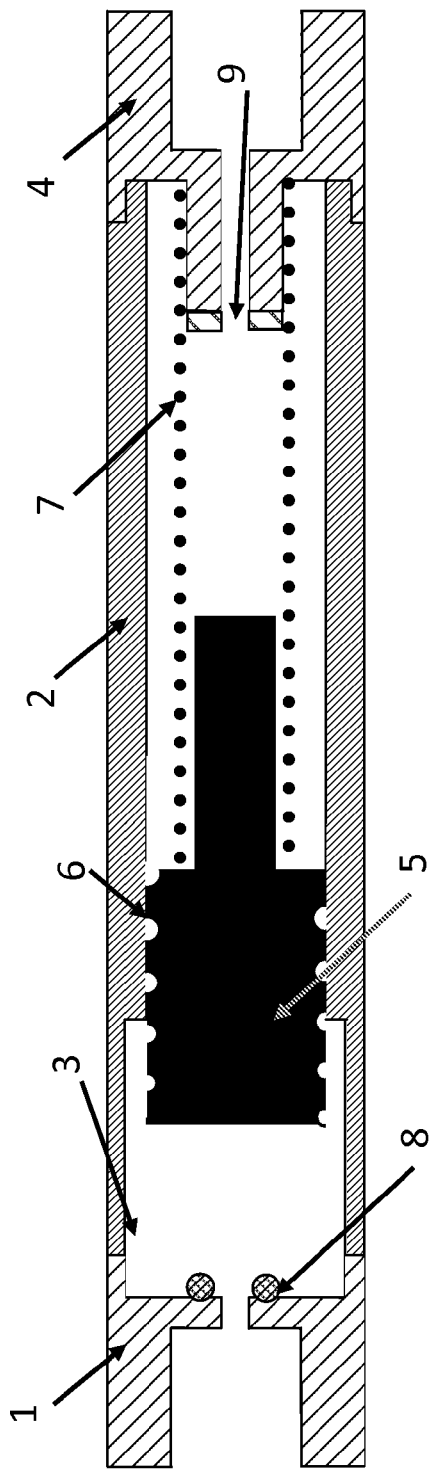
FIG. 12 illustrates an embodiment of the device comprising a channel having a variable depth and/or width.
Figure 13:
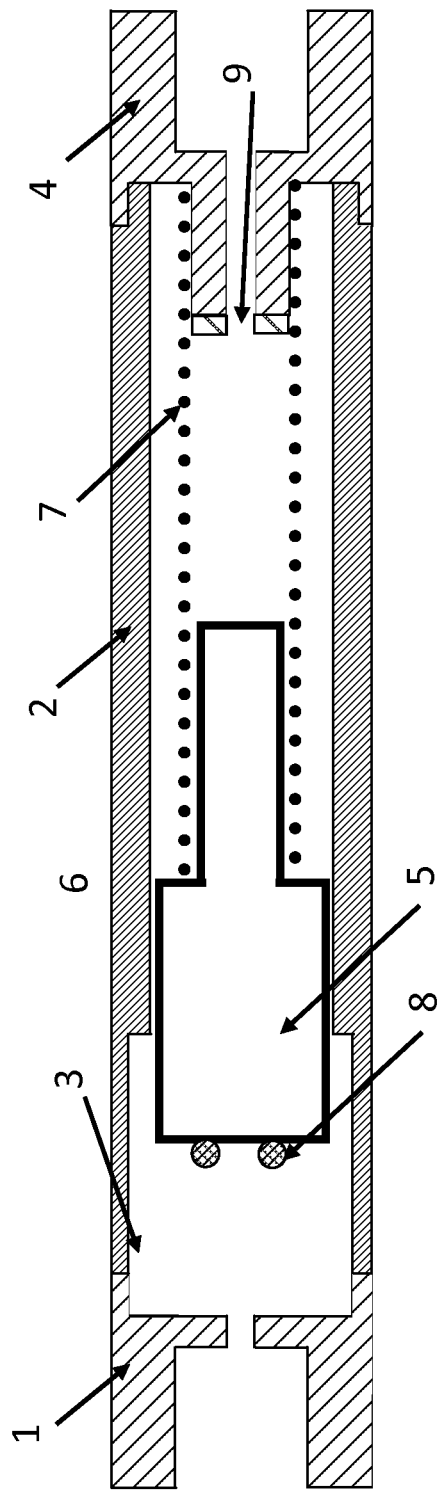
FIG. 13 illustrates an embodiment of the device comprising an elastomeric ring in the rod.
Figure 14:
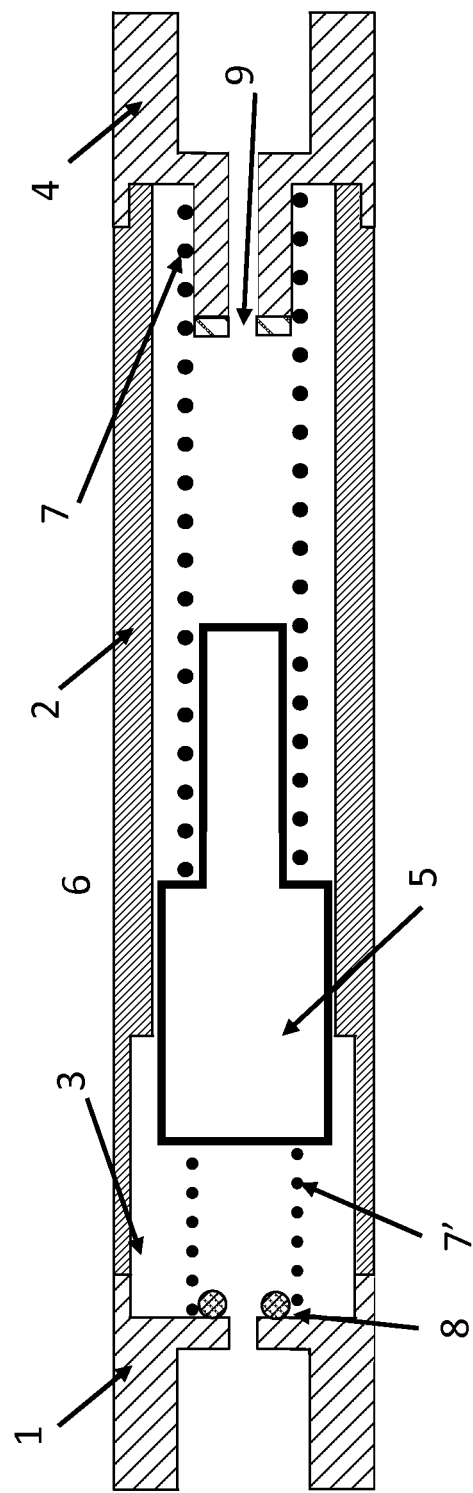
FIG. 14 illustrates an embodiment of the device comprising a second spring means (7').
Figure 15:
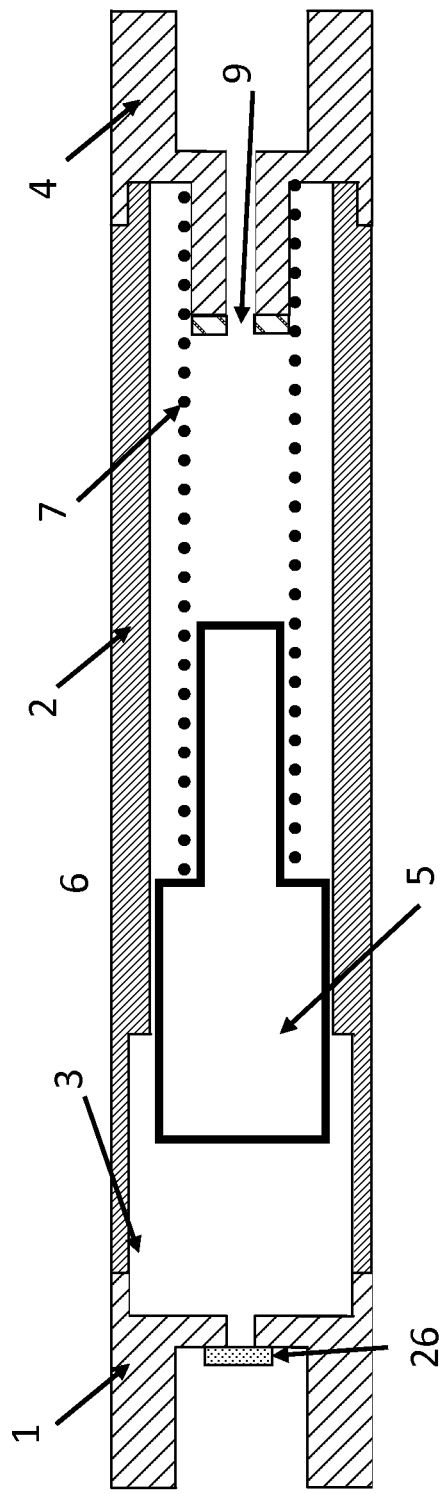
FIG. 15 illustrates an embodiment of the device comprising a particle filter (26).

The simplest way is to adjust the position of the spring support typically in the outlet connector. The adjustment of the spring preload can be done by screwing the outlet connector onto the cylinder up to preselected positions that correspond to different values of the valve opening pressure (see FIGS. 7 and 9). The adjustment can be done manually during the assembly or by external means, typically by using a rotary motor 22 coupled to the outlet connector 4 via a shaft 23. Additional o-rings 24 and 25 may be placed into the inlet and outlet connectors respectively to ensure the tightness after the screwing of said connectors onto the cylinder.

Figure 8:
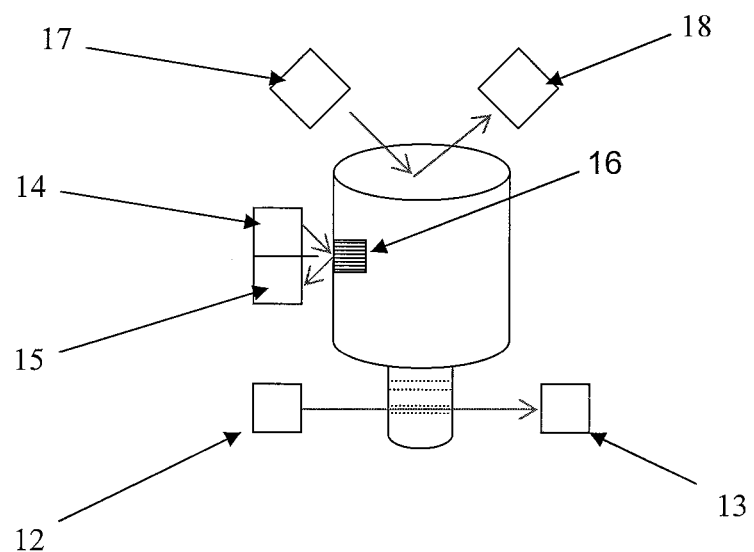
FIG. 8 illustrates schematically the principle of detectors used in the frame of the present invention.

The measurement of the rod position during the functioning is a good estimator of the pressure (if the rod is not blocked) e.g. by using Hall sensors in a magnetic circuit (rod with a magnetic core . . . ). FIG. 8 illustrates schematically the embodiment of detectors.

An optical source (e.g. a LED . . . ) and a photodiode can be used for the detection of the rod displacement. This can be used as threshold detection, typically in order to check that the rod is not blocked.

Holes should be drilled in the cylinder for the optical pathway. A light source 12 and a photodetector 13 are placed at 180° with respect to the cylinder 2 axis. At low pressure the optical pathway is free (only CSF liquid is present, see FIG. 3) and a signal is detected on the detector 13 while at high pressure the rod 5 masks the light and no signal is detected.

In a variant, an optical system can be a sensor comprising the LED 14 and the detector 15 in the same device. An optical scale 16 can be placed onto the rod 5 in order to modulate the light received by the detector 15. The position of the rod 5 is then derived from the analysis of the detector 15 signal.

In another variant, the top surface of the rod 5 can be used as a mirror that reflects the light of a source 17 (for example a LED) to a detector 18. The source 17 and the detector 18 should be placed at 180° with respect the cylinder axis.

The quantity of light received by the detector 13 depends on the rod position and could be calibrated in order to get the position of the rod. The angle of incidence of the emitted light should be adjusted to the stroke of the rod: a large incident angle is favourable in term of sensitivity but strongly limit the range of detection and vice versa.

A flowmeter (thermal . . . ), may be implemented before or after the device as long as the fluidic resistance of the sensor is lower than the regulator itself.

A pressure sensor, typically made of a flexible membrane mounted with strain gauges, one side connected to the inlet port and the other to the outlet port, could be implemented for estimated the differential of pressure in the device.

The flow meter or the pressure sensor is preferably monitored by a physician who can check the efficiency of the therapy (in case of a medical application) and therefore the good functioning of the device.

Preferably, all external parts of the shunt or accessory device are radiopaque or carry radiopaque markers. All parts of the shunt are identifiable via X-ray examination.

The shunt is made, for example, of titanium or iron which have an atomic number larger than calcium and therefore they can be directly identifiable via X-ray examination.

In addition, by design this device is sensitive to particles which can block the rod or make a channel obstruction.

The device should therefore preferably include:
- A filter (26) at the inlet
- A hydrophilic coating of the rod and the cylinder to prevent protein binding (eg PEG . . . )

The sensitivity to particles should be considered during the cleaning of the different parts and the assembly of the device in clean room.

By design the device has also the capability to be self-cleaning, since the constant move of the rod, typically when the patient wakes up or runs can help to expulse particles that block the rod against the cylinder.

The device has been designed to meet the typical characteristics of standard hydrocephalic shunts. The preferred external dimensions are 20 mm in length and 5 mm in diameter. These dimensions can be adapted typically to match to standard springs or machining tools. Many additional features can be implemented and its field of utilization can be extended to other applications than hydrocephalus treatment such as drug delivery requiring the same principle of functioning.

Of course, other dimensions may be envisaged for other applications of the device.

The main advantages of the device according to the invention are summarized below:
- Flow regulation
- Adjustable opening threshold
- Check valve
- Possibility to implement a shutdown system
- Possibility to have a free flow at high pressure
- Possibility to have a flow restriction at high pressure
- Standard machining techniques (undercutting)
- Low cost system
- Simple design and redesign
- Possibility to adjust the spring to the machined elements
- Simple assembly and test
- Assembly reversible
- Possibility to implement position sensor for the rod
- Large capability for specific flow regulation profile As mentioned above, the main description of the present invention has been made in the frame of a hydrocephalus shunt to drain CSF but is it not limited to this specific application and other applications may be envisaged, in the medical or in other fields.

In the medical field, the device may be implanted or not and may be made of biocompatible materials, if necessary. Of course, according to circumstances, other materials might be envisaged. Also other values are possible, depending on the application, and the examples given herein are only illustrative and non limitative.

In the above description, only one spring means 7 working in compression has been shown. It is however also possible to use a spring means working in extension (rather than compression) and place it at the inlet side of the device.

This variant however does not change the principle and mode of functioning of the device and the above description applies correspondingly in this case as a skilled person will understand.

It is also possible to use two spring means (7 and 7'), one on each side of the rod to form a damping means is case of sudden changes in the pressure. The characteristics of this damping must in any case be adapted to not interfere with a proper functioning of the device. To this effect, it might be necessary to adapt other characteristics (preload of the other spring for example) to this additional 25 spring. As mentioned above, the spring means may be preloaded for example in order to ensure a tightness of the regulator if the difference of pressure is lower than a certain predetermined threshold. Of course, this might be fixed or variable to adjust the threshold. For example, one may use specific means to adjust the preload of the spring means, said means being externally adjustable.

In all cases the spring(s) can be attached by to the rod and/or the cylinder and/or the connector(s). In the FIGS. 2 and 3, the compression spring is simply guided by both the rod (19) and the outlet connector (20), making the mounting of the device simpler but an attachment may be envisaged. The spring(s) can be also guided by the cylinder internal surface.

One may also use specific means to move the rod and change its position. This would allow for example to test the device or force the rod to move in case of blocking.

The materials used can be of any type suitable for the intended use of the regulator. They are biocompatible in case of an implantable device. They may undergo specific treatments, for example a surface hardening process to ensure a precise functioning and may also be coated with agents, for example hydrophilic agents.

The invention claimed is:

1. A passive fluid flow regulator comprising
   at least a cylinder (2) with a fluid inlet connector (1) for receiving fluid at an inlet pressure and a fluid outlet connector (4) for delivering fluid,
   at least one chamber (3),
   a rod (5) in said cylinder with a first side submitted to the inlet pressure and a second side submitted to the outlet pressure generating a net force counter-balanced by at least one spring means (7) acting on the first or the second side of said rod (5) against said inlet pressure,
   wherein a fluidic pathway, which includes a channel formed between said rod (5) and said cylinder (2), extending from the first side to the second side of the rod, on a surface of the rod or an inner surface of the cylinder, is formed between said rod (5) and said cylinder (2) as a major fluidic resistance of the regulator, wherein a change of the inlet pressure induces a move of the rod (5) along an axis of the cylinder thereby increasing the fluidic resistance of said fluidic pathway due to an increase of the length of said pathway, wherein the fluidic resistance of said pathway varies with the applied pressure at the inlet in a predefined range of pressure, inducing a regulated flow rate in the considered range of pressure.

2. A regulator as defined in claim 1, wherein said fluidic pathway is formed directly in a space between the outside surface of the rod (5) and the inner surface of the cylinder (2).

3. A regulator as defined in claim 1, wherein the rod (5) has a cavity (10), wherein said cavity is filled with a gas, wherein the volume of the cavity (10) is adjusted to make the density of the rod (5) equal to the density of the fluid, such that it counterbalances its own weight by Archimedes force and makes the system independent from its spatial orientation and reduces the friction forces.

4. A regulator according to claim 1, wherein the position of the rod (5) can be changed by external means.

5. A regulator as defined in claim 1, wherein the surface of the rod (5) and/or of the cylinder (2) or both have been submitted to a hardening process.

6. A regulator as defined in claim 1, wherein the regulator comprises materials that are biocompatible.

7. A regulator as defined in claim 1, wherein it comprises a second spring means as a damper or shock absorber.

8. A regulator as defined in claim 1, wherein the outlet is occluded if the pressure exceeds a predefined safety pressure.

9. A regulator as defined in claim 1, wherein the fluidic resistance of the device remains constant after a predefined operating pressure.

10. A regulator as defined in claim 1 wherein it comprises a particle filter.

11. A regulator as defined in claim 1, wherein parts of the regulator in contact with the fluid are coated with hydrophilic agents.

12. A regulator as defined in claim 1, wherein the flow rate is regulated in the range of pressure 0-40 mbar according to a predefined profile, wherein the mean flow rate in said pressure range varies from 5 ml/h to 50 ml/h, wherein the flow rate at higher pressures increases with said pressure, wherein the valve is a check-valve with an opening threshold that can be adjusted between 0 to 40 mbar.

13. A regulator as defined in claim 1, wherein there is no flow rate by applying a pressure lower than the opening pressure of the regulator, wherein the flow rate versus pressure characteristic shows 3 successive phases by increasing the pressure above said opening pressure, the flow rate respectively increasing, decreasing and finally increasing again.

14. A regulator as defined in claim 1, wherein the flow rate is regulated in the range 0-50 mbar, wherein the flow rate exhibits a maximum at a pressure lower than 50 mbar, and wherein the flow rate exhibits a decrease and a minimum by increasing the pressure between said pressure and 50 mbar, wherein the flow rate exhibits an increase by increasing the pressure above 50 mbar.

15. A regulator as defined in claim 1, wherein the spring (7) is preloaded, pushing the rod (5) against an elastomeric ring (8) in the inlet connector or in the rod and ensuring the tightness of the valve if the difference of pressure between the inlet and the outlet is lower than the threshold value defined by the preload of the spring (7).

16. A regulator, according to claim 15, wherein the preload of the spring (7) is adjustable by external means (22,23).

17. A regulator as defined in claim 1 wherein the regulator comprises position sensors to determine a position of the rod in said cylinder.

18. A regulator as defined in claim 17, wherein said sensors are optical sensors and/or magnetic sensors and/or pressure sensors.

19. A regulator as defined in claim 17, wherein the sensors are powered and monitored by external means.

20. A regulator as defined in claim 1, wherein said fluidic pathway is formed by at least one channel (6) in said rod (5) or in said cylinder (2) or in both.

21. A regulator as defined in claim 20, wherein the channel (6) is parallel to the axis of the cylinder (2) or wherein said channel (6) has the shape of a helix with a pitch.

22. A regulator as defined in claim 21, wherein said channel (6) has a constant depth and width and/or a constant pitch such that the flow rate in the valve is constant in a predefined range of pressures.

23. A regulator as defined in claim 21, wherein said channel (6) has a variable depth and/or width and/or pitch such that the flow rate in the valve is variable.

* * * * *